(12) United States Patent
Ahmed

(10) Patent No.: US 6,235,725 B1
(45) Date of Patent: May 22, 2001

(54) METHODS AND COMPOSITIONS FOR THE PREVENTION OF TOLERANCE TO MEDICATIONS

(75) Inventor: Tahir Ahmed, Coral Gables, FL (US)

(73) Assignee: Baker Norton Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 09/362,540

(22) Filed: Jul. 28, 1999

Related U.S. Application Data

(60) Provisional application No. 60/106,507, filed on Oct. 30, 1998.

(51) Int. Cl.$^7$ ..................................................... A61K 31/70
(52) U.S. Cl. ................................. 514/56; 514/23; 514/53; 514/54; 514/653; 514/826
(58) Field of Search ................................. 514/53, 54, 56, 514/653, 826, 23

(56) References Cited

U.S. PATENT DOCUMENTS

| | | |
|---|---|---|
| 4,933,326 | 6/1990 | Bianchini et al. . |
| 5,032,679 | 7/1991 | Brandley et al. . |
| 5,049,389 | 9/1991 | Radhakarishnan . |
| 5,192,548 | 3/1993 | Velasquez et al. . |
| 5,380,716 | 1/1995 | Conrad et al. . |
| 5,674,860 * | 10/1997 | Carling et al. ........................ 514/171 |
| 5,709,884 | 1/1998 | Trofast et al. . |
| 5,714,376 | 2/1998 | Sasiskharan et al. . |
| 5,736,124 | 4/1998 | Akehurst et al. . |
| 5,817,293 | 10/1998 | Akehurst et al. . |
| 5,874,063 | 2/1999 | Briggner et al. . |

OTHER PUBLICATIONS

Sheffer, et al. (1993) *Med. Care 31*:MS20.
Am. Rev. Respir. Dis. (1987) 136:225–244.
Hargreave, et al. (1986) *J. Allergy Clinical Immunol.* 83:1013–1026.
Fuci, et al. (1998) *Harrison's Principals of Internal Medicine 14th Ed.*, pp. 1419–1426.
Barnes, et al. (1990) *Am. Rev. Respir. Dis.* 141:S70–S76.
Woolock, et al. (1996) Am. Respir, Crit, Care. 153:1481–1488.
Volcheck, et al. (1998) *Postfrad Med.* 104(3):127–136.
Palmer, et al. (1994) *New Eng. J. Med.* 331:1314–1319.
Bhagat, et al. (1995) *Chest 108*: 1235–1239.
Lipworth, et al. (1995) *Lancet 346*:201–206.
Woolcock (1995) *Eur. Respir. Rev.* 5:(27)142–145.
Kalra, et al. (1996) *Chest 109*:953–56.
Hausdorff, et al. (1990) *FASEB J 4*:2881–2889.
Liggert, et al. (1992) *J. Biol. Chem.* 267:4740–4746.
Schlelricher, et al. (1993) *Proc. Nat'l. Acad. Sci. USA* 90:1420–1427.
Turki et al. (1995) Am. Physiol. 269(13):L709–L714.
Ahmed, et al. (1992) *Am. Rev. Respir. Dis.* . 145:566–570.
Lucio, et al. (1992) *Amer. Physiol Soc.* 73(3):1093–1101.
Ahmed, et al. (1993) *N. Eng. J. Med.* 329:90–95.
Ahmed, *Respiratory Drug Delivery IV*, 55–63.
Lane, et al. (1989) *Chemical and Biological Properties, Clinical Applications.*
Goodwin & Gilman (1996) *The Pharmacological Basis of Therapeutics*, 9$^{th}$ Ed.
Harrison's *i Supra* at pp. 1167–1176.
Goodman's & Gilman's *Supra* at pp. 664–665.
Goodman's & Gilman's *supsra* at Chapter 7.
Fisher and Tiemann (1984) Ber Dtsch. Chem. Ges. 27:138–147.
Foster Chem. Ind.627 (1955) and Shively and Conrad (1976) *Biochemistry 15*:3932–3942.
Linker, et al. (1972) *Methods of Enzymology*, Ginsburg Ed., Academic Press, New Yorks pp. 902–911.
*Remington's Pharmaceutical Sciences* (1990) 18th., Ed., Gennaro, Mack Publishing Co., Easton PA.
*Remington: The Science and Practice of Pharmacy* (1995) Lippincott, Williams & Wilkins.

* cited by examiner

*Primary Examiner*—Elli Peselev
(74) *Attorney, Agent, or Firm*—Simona A. Levi-Minzi

(57) ABSTRACT

The present invention pertains to the identification of moieties and methods of using the same for preventing tolerance to bronchodilators. More specifically, the present invention pertains to the identification of compositions and methods which are capable of preventing tolerance to $\beta_2$-adrenergic agonists. The methods and compositions according to the invention are also useful as analytical tools for functional studies and as combination therapeutic tools.

35 Claims, 2 Drawing Sheets

METHODS AND COMPOSITIONS FOR THE PREVENTION OF TOLERANCE TO MEDICATIONS

CROSS-REFERENCE TO RELATED APPLICATIONS

This application claims the priority of provisional application Serial No. 60/106,507, filed Oct. 30, 1998.

BACKGROUND OF THE INVENTION

1. Field of the Invention

The present invention relates to methods and compositions for the prevention of tolerance to medications such as pharmaceutical agents. In particular, the present invention comprises compositions and methods for the prevention of tolerance to medications used in the treatment of asthma and related pathologies.

2. Summary of the Related Art

More than fifteen million persons in the United States suffer from asthma and related inflammatory lung diseases. The number of persons with asthma is increasing both in the United States and worldwide. The morbidity associated with asthma makes it a major medical condition. Asthma is the most common chronic disease of childhood and the leading cause of school absence. Asthma in humans results in an estimated 27 million patient visits, 6 million lost workdays, and 90.5 million days of restricted activity per year. In addition to its morbidity, the mortality rate for asthma is growing worldwide. Additionally, asthmatic reactions are a growing problem for animals. In particular, the horse racing industry is affected by horses that suffer from asthmatic reactions (for a general review of asthma see Sheffer et al., The National Asthma Education Program: Expert panel report guidelines for the diagnosis and management of asthma, Med. Care 31:MS20 (1993)).

Clinically, asthma is a chronic obstructive pulmonary disease characterized by a usually reversible airway obstruction, airway inflammation and increased airway responsiveness to non-specific stimuli (see Standards for the Diagnosis and Care of Patients with Chronic Obstructive Pulmonary Disease (COPD) Am. Rev. Respir. Dis 136:225–244 (1987)). The airway obstruction during an asthma attack is due to the combination of bronchospasm (airway smooth muscles contraction), increased mucous secretion, edema of airway mucosa due to increased vascular permeability, cellular infiltration of the airway walls, and injury to airway epithelium. Hargreave et al., J. Allergy Clinical Immunol. 83:1013–1026 (1986) teaches that asthma may be triggered by a variety of causes such as allergic reactions, a secondary response to infections, industrial or occupational exposures, ingestion of certain chemicals or drugs, exercise, and vasculitis. *Harrison's Principles of Internal Medicine* (14$^{th}$ Edition Fauci et al. Eds., McGraw-Hill, New York (1998), pages 1419–1426), teaches that in many cases, there are two phases to an allergic asthma attack, an early phase and a late phase which follows 4–6 hours after bronchial stimulation. The early phase includes the immediate inflammatory response including the reactions caused by the release of cellular mediators from mast cells. The late phase reactions develop over a period of hours and are characterized histologically by an early influx of polymorphonuclear leukocytes and fibrin deposition followed later by infiltration of eosinophils. Late phase reactions and airway inflammation lead to prolonged airway hyper-reactivity and asthmatic exacerbations that may last from days to months in some subjects. Barnes et al., Am. Rev. Respir. Dis. 141:S70–S76 (1990) teaches that hyper responsiveness of the airways to nonspecific stimuli is a hallmark of this disease. Hence, at the present time, the general goals of drug therapy for asthma are prevention of bronchospasm and control of airway hyperactivity or hyper responsiveness, an indication of airway inflammation.

Conventional treatments have been predicated on the strict avoidance of all allergens, which is inherently difficult to achieve, and on therapeutic regimens based on pharmacological agents having unfortunate side effects and suboptimal pharmacokinetic properties. Hence, theophylline (a methylxanthine) for example, is characterized by substantial variability in the absorbance and clearance of theophylline. Woolock et al., Am. Respir. Crit. Care Med. 153:1481–1488 (1996) teaches that corticosteroids are used to treat late-phase and airway hyperactivity reactions. Volcheck et al., Postgrad Med. 104(3):127–136 (1998) discloses the use of cromolyn to prevent both the early and late phases of asthma inflammatory reactions. Cromolyn however, is only effective in preventing the onset of an asthma reaction if given prior to an asthma attack.

Alternative widespread treatment approaches have relied on the administration of adrenergic agonists which mimic the physiological effects of the adrenal medullary hormones and neurotransmitters of the sympathetic nervous system. $\beta_2$-adrenergic agonists represent important therapeutic agents in the treatment of asthma. Palmer et al., New Engl. J. Med. 331:1314–1319 (1994) teaches that salmeterol is a long-acting $\beta_2$ adrenergic agonist that has been introduced as an adjunct to anti-inflammatory therapy in asthma management. Due to its slow onset but prolonged duration of action, the recommendation is to prescribe salmeterol for regular use, along with salbutamol for acute relief of break-through symptoms. The administration of $\beta_2$-adrenergic agonists, such as salmeterol, has been found to down-regulate $\beta_2$-adrenergic receptors. Bhagat et al. Chest 108:1235–1238 (1995) teaches that regular or prolonged use of $\beta_2$-adrenergic agonists is associated with poor control of asthma, increase in airway hyper responsiveness to allergen, and reduced protection against bronchoconstriction induced by exercise, histamine, methacholine and allergens challenge. Furthermore, recent reports suggest that regular use of $\beta_2$-agonists may also result in mild tolerance to bronchodilator response.

There are also side effects that result from treatment with adrenergic agonists because the adrenergic agonists are generally not selective for only the $\beta_2$-receptors, but also effect $\beta_1$-receptors causing cardiac stimulation. $\beta_2$-adrenergic agonists can be used for treatment of bronchospasm, but have no effect on airway inflammation or bronchial hyperactivity. In fact, chronic use of $\beta_2$-adrenergic agents alone, by down regulation of $\beta_2$-receptors, may worsen bronchial hyperactivity.

The development of tolerance is exemplified by treatment with the long-acting $\beta_2$-agonist, salmeterol. Salmeterol is a long-acting $\beta_2$-agonist used in the treatment of mild to moderate asthma. Several studies have shown that regular treatment with salmeterol results in loss of the bronchoprotection against different stimuli, such as exercise, methacholine, histamine. A recent study reported that tolerance to the bronchoprotective effect of salmeterol can occur as soon as after the third dose of salmeterol (see Bhagat et al., Chest 108:1235–39 (1995)). Furthermore, Lipworth, et al., Lancet 346:201–206 (1995) showed that chronic use of salmeterol results in reduction of the bronchodilator response to salbutamol.

Recent studies have sought to find approaches to counter tolerance. One approach has been that of combining bronchodilators associated with rapid reduction in bronchoprotective effect, such as salmeterolor formoterol, with corticosteroids (see Woolcock, Eur. Respir. Rev. 5:(27)142–145 (1995) and U.S. Pat. Nos. 5,049,389, 5,192,548, 5,674,860, 5,709,884, 5,736,124, 5,817,293, and 5,874,063). Despite the enthusiasm in the field, evidenced by the many reports available in the literature, such approaches have thus far failed. It has been shown that inhaled corticosteroids do not prevent the development of tolerance to the bronchoprotective effect of salrneterol (see Kalra et al. Chest 109:953–56 (1996). In contrast, high dose systemic glucocorticosteroids may prevent the tolerance to the bronchodilator effect of $\beta_2$-agonist.

In an attempt to counter tolerance, investigators have sought to elucidate the mechanism underlying such phenomenon. Several mechanisms have been proposed for the down-regulation of the $\beta_2$-adrenergic receptors. Hausdorff et al., FASEB J. 4:2881–2889 (1990) teach that tolerance stems from molecular mechanisms underlying rapid beta adrenergic receptor (hereinafter, "$\beta$AR") desensitization which are in turn due to an alteration in the functioning of $\beta$AR that uncouples the receptors from the stimulatory G protein Gs. This uncoupling phenomenon involves phosphorylation of $\beta$AR by at least two kinases, protein kinase A (hereinafter, "PKA") and the $\beta$AR kinase (hereinafter, "$\beta$ARK"), which are activated under different desensitizing conditions. Receptor phosphorylation by the two kinases has also been shown to lead to desensitization of the receptor response via distinct biochemical mechanisms (see also, Liggett et al., J. Biol. Chem. 267:4740–4746 (1992); Schlericher et al., Proc. Natl. Acad. Sci. USA 90:1420–1424 (1993) and Turki et al., Am Physiol. 269(13):L709–L714 (1995)).

From a practical standpoint, the down-regulation of the $\beta_2$-adrenergic receptors and hence, tolerance, often results in the administration of higher dosages of the $\beta_2$-adrenergic agonist exposing the asthmatic patient to greater side effects. In some patients, tolerance may even reach the stage at which the patient is wholly unresponsive forcing the practitioner to adopt even less desirable approaches.

Recent reports have identified treatment regimens for antigen induced asthma based on heparin. Ahmed et al., Am. Rev. Respir. Dis. 145:566–570 (1992) for example teaches that the use of glycosaminoglycan heparin prevents bronchoconstrictor responses induced by stimuli that produce immunologic mast-cell degranulation in sheep, without attenuating agonist-induced bronchoconstriction. Similarly, Lucio et al., Amer. Physiol. Soc. 73(3):1093–1101 (1992) teaches that immunologic mast cell-mediated responses and histamine release are attenuated by heparin. Other work in the field has also demonstrated the prevention of exercise induced asthma with inhaled heparin (see for example, Ahmed et al., N. Eng. J. Med. 329:90–95 (1993) and Ahmed, Respiratory Drug Delivery IV, 55–63).

Heparin has been used for a variety of purposes. Lane et al. *Chemical and Biological Properties, Clinical Applications*, Edward Arnold Ed. London (1989) teaches that heparin is a highly sulfated, unbranched glycosaminoglycan used in the clinical practice as an anticoagulant agent. This activity results from heparin's ability to bind some of the residues of antithrombin III (AT-III), accelerating the neutralization by AT-III of activated clotting factors and preventing the conversion of prothrombin to thrombin. Larger amounts of heparin can inactivate thrombin and earlier clotting factors, preventing conversion of fibrinogen to fibrin. Heparin is synthesized in mast cells as a proteoglycan and is particularly abundant in the lungs of various animals. Heparin is not a specific compound of fixed molecular weight, but is actually a heterogeneous mixture of variably sulfated polysaccharide chains composed of repeating units of D-glucosamine and L-iduronic acid. Despite the extensive heparin literature for selected asthma applications, to date the use of heparin to address bronchodilator induced tolerance has not been investigated.

Thus, there is a long felt need for methods and compositions for the treatment of asthma and related pathologies. Such methods should address the shortcomings of traditional therapeutic approaches. More specifically, there is a need for novel modalities and compositions capable of preventing the tolerance that is developed by use of traditional bronchodilators. Such novel approaches should prevent the down-regulation of $\beta_2$-adrenergic receptors in response to the use of $\beta_2$-adrenergic agonists. Moreover, there is a need for methods and compositions capable of preventing tolerance developed in response to use of $\beta_2$-adrenergic agonists for the treatment of asthma which are easily administered, and which minimize side effects as compared to current protocols. Ideally such compositions should be easily administered (e.g. self-administrated inhalation).

SUMMARY OF THE PRESENT INVENTION

The present inventor has devised novel compositions and methods effective in preventing development of tolerance to pharmacological agents. Surprisingly, these approaches have been found to be particularly effective in preventing the development of tolerance in the use of $\beta_2$-adrenergic agonists as well as being easily administered. Such methods and compositions therefore, represent long awaited approaches to the management of asthma and related pathologies, which address the shortcomings of traditional regimens.

In a first aspect the invention provides novel and improved methods useful for preventing tolerance to medications, such as to bronchodilators, used in the treatment of asthma and related pathologies. This aspect of the invention thus, also sets forth improved methods useful for treating asthma and related pathologies in a mammal, including the administration of bronchodilators in conjunction with effectors as described infra.

In a second aspect the invention provides analytical tools for the elucidation of the activation and inhibition of the adrenergic receptor activity. The invention provides novel tools to assess the role played by polyanions and their interaction with bronchodilators in the modulation of the activity of $\beta$ARK. More specifically, the invention sets forth compositions and methods useful to evaluate the ability of mucopolysaccharides, such as heparin, to inhibit the phosphorylation of the adrenergic receptor by $\beta$ARK. Such tools can be used as "probes" of the physiological function of $\beta$ARK and of the interplay with agonist-specific desensitization of the receptor-coupled adenyl cyclase system.

In a third aspect the invention provides novel compositions useful for preventing tolerance to medications, such as to bronchodilators, used in the treatment of asthma and related pathologies. This aspect of the invention also provides novel compositions useful for treating asthma and related pathologies in a mammal, including the administration of bronchodilators in conjunction with effectors as described infra.

DETAILED DESCRIPTION OF THE PREFERRED EMBODIMENTS

Figure 1:
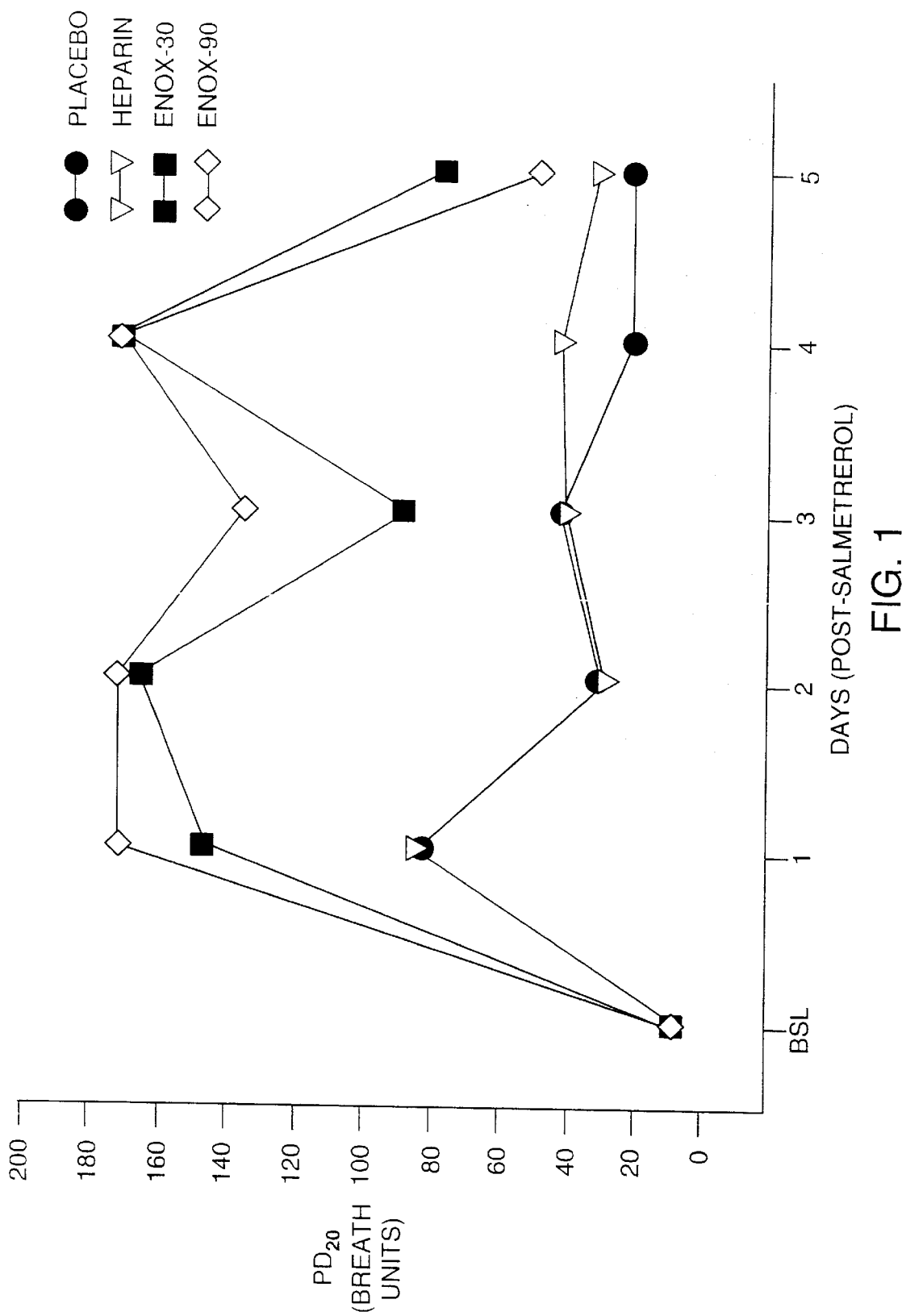
FIG. 1 is a graphic representation showing the ability of a representative, nonlimiting, bronchodilator (salmeterol) used in conjunction with a representative, nonlimiting, effector (heparin) according to the invention to prevent tolerance to bronchodilators. Data are shown as the cumulative provocating dose of methacholine in breath units, which caused a 20% decrease in $FEV_1$ ($PD_{20}$). $PD_{20}$ was determined for the baseline day (BSL) and after the $1^{st}$, $3^{rd}$, $5^{th}$, and $7^{th}$ dose of salmeterol (42 μg BID), following pretreatment with inhaled heparin (80,000 units BID) or placebo. The first dose of salmeterolcaused a marked increase in $PD_{20}$-methacholine on day 1, showing bronchoprotection. Lesser bronchoprotection was observed after the $3^{rd}$-$7^{th}$ doses of salemeterol (days 2-4), indicating development of tolerance. As shown tolerance was prevented by inhaled heparin. Note the symbol (+) is used to denote values significantly different from day 1 ($P<0.05$) and (*) is used to denote values significantly different from placebo ($P<0.05$).

The present invention pertains to the identification of moieties and methods of using the same for preventing tolerance to bronchodilators. More specifically, the present invention pertains to the identification of compositions and methods which are capable of preventing tolerance to $β_2$-adrenergic agonists. The methods and compositions according to the invention are also useful as analytical tools for functional studies and as therapeutic tools. Surprisingly, these approaches have been found to be particularly effective in preventing tolerance in the use of $β_2$-adrenergic agonists as well as being particularly easily administered. The compositions and modalities described herein also provide long sought therapeutic approaches to the treatment of asthma and of related pathologies in mammals.

More specifically, the present invention comprises compositions that prevent the loss or diminution of bronchoprotective effect by $β_2$-adrenergic agonists. The invention also sets forth novel combination approaches offering novel and improved pharmacological properties for the treatment of asthma and of related pathologies in a mammal. The patents and scientific literature referred to herein establish the knowledge of those with skill in the art and are hereby incorporated by reference in their entirety.

In a first aspect the invention provides novel and improved methods useful for preventing tolerance to medications, such as to bronchodilators, used in the treatment of asthma and related pathologies. This aspect of the invention thus, also sets forth improved methods useful for treating asthma and related pathologies in a mammal, including the administration of bronchodilators in conjunction with effectors.

Hence, the invention sets forth a method for preventing tolerance in a mammal to medications, such as to bronchodilators used in the treatment of asthma and related pathologies, including the step of administering therapeutically effective amounts of a bronchodilator and of an effector for a therapeutically effective period of time.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, $9^{th}$ Ed., McGraw Hill Companies Inc., New York (1996).

Any suitable materials and/or methods known to those of skill can be utilized in carrying out the present invention. However, preferred materials and methods are described. Materials, reagents and the like to which reference is made in the following description and examples are obtainable from commercial sources, unless otherwise noted.

The methods of the present invention are intended for use with any mammal which may experience the benefits of the methods of the invention. Foremost among such mammals are humans, although the invention is not intended to be so limited, and is applicable to veterinary uses.

The term "prevent" and any variation thereof are used to include partial as well as complete inhibition. Practically, "prevention" according to the invention may be detected as a positive change in the effectiveness of a bronchodilator administered in connection with an effector of the invention as compared to the use of the bronchodilator without an effector. The term "bronchodilator" as used herein, denotes an active moiety capable of causing an increase in caliber of a bronchus or bronchial tube. Use of bronchodilators in the treatment of asthma and related pathologies is well-known in the art, and those known compounds are included within the scope of the present invention (see for example *Harrison's* supra, at pages 1167-1176).

Preferred examples of bronchodilators of the invention therefore include, without limitation, specific β-adrenergic agonists, anticholinergic agents, and theophylline (for a general discussion of bronchodilators see, Goodman and Gilman's supra at pages 664-665).

In a preferred embodiment of the invention, the specific β-adrenergic agonists are $β_2$-adrenergic agonists. Nonlimiting representative examples of $β_2$-adrenergic agonists include, salmeterol, formoterol, bambuterol, alituerol, terbutaline, pirbhvteiol, bitolterol, metaproterenol, isoetharine, and isoproterenol (see, Goodman and Gilman's supra, at pages 213-217).

In some preferred embodiments of the invention, the anticholinergic agent is ipratropium bromide (hereinafter "ipratropium"), tiotropium bromide, or oxytropium bromide. In other preferred embodiments of the invention, the bronchodilator is theophylline and the related drug aminophylline. (see, Goodman and Gilman's supra, Chapter 7).

For purposes of the invention the term "effector" is used to refer to a moiety which when administered in conjunction with the bronchodilator(s) according to the invention is capable of preventing tolerance to one or more of the bronchodilators administered therewith. In certain preferred embodiments, the effectors of the invention are useful for the treatment of asthma and related pathologies in a mammal.

Nonlimiting representative examples of effectors according to the invention include polyanions, such as for example polysaccharides. Polysaccharides which may be used as effectors in preferred embodiments according to the invention include, without limitation, polysaccharides such as dextran, heparin, heparan sulfate, dermatan sulfate, chondroitin sulfate, and/or other glycosaminoglycans and mucopolysaccharides. In a particularly preferred embodiment of the invention, the effector is a sulfated polysaccharide (e.g. N-Sulfation). In a more preferred embodiment, the effector is an oligomer comprising from 1 to about 10 sugar residues. In a most preferred embodiment, the effector is an sulfated tetrasaccharide.

In a particularly preferred embodiment, the effector is heparin. The term "heparin" as used herein includes selected fractions of heparin or mixtures comprising more than one heparin fraction that are effective in the methods and compositions of the present invention.

Fractions of heparin can be prepared by chemical, enzymatic or synthetic processes well known in the art. Chemical depolymerization has been carried out in many different ways (see for example, Fisher and Tiemann, Ber. Dtsch. Chem. Ges. 27:138–147 (1984) and Foster, Chem. Ind. 627 (1955) and Shively and Conrad, Biochemistry 15:3932–3942 (1976). Such methods include depolymerization by nitrites at low pH, by alkaline β-elimination following esterification of uronic acids or by oxidative methods using peroxides or periodate. After depolymerization with nitrites, the anhydromannose at the reducing end of the heparin and oligosaccharide fragments are usually reduced to anhydromannitol or oxidized to anhydromannonic acid. Alkaline β-elimination results in 4,5-unsaturation in the nonreducing end of the heparin fragments and oligosaccharides produced. These groups may be reduced using catalytic hydrogenation or the whole 4,5-unsaturated monosaccharide can be eliminated with mild acid treatment or metal-containing reagents such as mercury salts. These treatments yield heparin fragments and oligosaccharides that have an uneven number of saccharide units. Alternatively the depolymerization of heparin can be achieved using enzymatic processes using commonly known heparinases, especially bacterial heparinases. Hence, U.S. Pat. No. 5,714,376 teaches the production and use of heparinase preparations isolated from *Flavobacterium Heparinum* (see also Linker et al., Methods of Enzymology, Ginsburg Ed., Academic Press, New York, (1972), pp. 902–911). Generally, the enzyme cleaves the heparin chain between the anomeric carbon of an N-sulfate-glucosamine residue and the preceding uronic acid unit that follows. The cleavage of heparin using enzymatic processes can produce a mixture of oligosaccharides, including di-, tetra-, hexa- and octasaccharides. The oligosaccharides so produced have a two-fold degree of polymerization and are terminated at the nonreducing end by an unsaturated uronic acid. These end groups may be reduced as described above for alkaline β-elimination.

In a preferred embodiment of the invention, the initial starting material is porcine or bovine intestinal mucosal or lung heparin. The present invention contemplates use of any material, including porcine, bovine or other animal sources, as the heparin source material.

It is to understood that the term heparin includes all the molecular weight fractions of heparin, including ultra low molecular weight (ULMWH), low molecular weight heparin (LMWH), and heparin fractions with molecular weights ranging from approximately 1,000 Daltons to approximately greater than 40,000 Daltons. The term "heparin" also encompasses heparin polysaccharide fragments including but not limited to any oligomeric form. In preferred embodiments of the invention the heparin oligomers are dimers, trimers, tetramers, pentamers, hexamers, septamers, octamers, nanomers or decamers. In most preferred embodiments, the heparin oligomers are tetramers.

One of skill in the art will appreciate that in some embodiments of the invention where the effector is ULMWH, it has substantially no anticoagulant activity. Similarly, in other embodiments, where the effector is LMWH, it has substantially no anticoagulant activity.

The effector of the invention may be fully N-sulfated, partially N-sulfated, O-sulfated, partially O-sulfated, or hypersulfated. In a preferred embodiment from about 5% to about 100% of the residues are N-sulfated. In a more preferred embodiment from about 30% to about 75% of the residues are N-sulfated. In an embodiment from about 5% to about 100% of the residues are O-sulfated. In a more preferred embodiment from about 30% to about 75% of the residues are O-sulfated. The term "hypersulfated" means sulfation of a residue of the effector which is not naturally sulfated resulting in increased charge density. The preparation of sulfated heparin and sulfated heparin fractions is well known in the art.

Though not wishing to be bound by any particular theory, it is proposed that the down regulation of $\beta_2$-adrenergic receptors occurs by the following pathway. Phosphorylation of $\beta_2$-adrenergic receptors by $\beta_2$-adrenergic kinase ($\beta$ARK) and protein kinase A (PKA) cause uncoupling of these receptors. In vitro studies have shown that heparin blocks the action of the $\beta$ARK, while glucocorticosteroids are ineffective. The present invention surprisingly finds that inhaled heparin, by theoretically inhibiting $\beta$ARK, prevents the salmeterol induced down-regulation of $\beta_2$-receptors in vivo.

In a preferred embodiment of the invention more than one effector is administered. In some embodiments, more than one type of polysaccharide (such as for example a heparin fraction and dextran) are administered. Similarly, in a preferred embodiment more than one bronchodilator is administered. Thus, for example in a more preferred embodiment a $\beta_2$-agonist and an anticholinergic are administered. In a most preferred embodiment of the invention, a combination formulation containing a mixture of ipratropium and albuterol are administered in conjunction with an effector according to the invention.

The bronchodilators and effectors according to the invention may optionally be formulated with any of the well known pharmaceutically acceptable carriers including diluents and excipients (see *Remington's Pharmaceutical Sciences*, 18$^{th}$ Ed., Gennaro, Mack Publishing Co., Easton, Pa. (1990) and *Remington: The Science and Practice of Pharmacy*, Lippincott, Williams & Wilkins (1995)). Formulations according to the invention thus may contain one or more bronchodilator(s), one or more additional effector(s), as well as any other pharmacologically active ingredient.

The designation "asthma and related pathologies" is used to refer to a condition predominantly inflammatory in nature with associated bronchospasm. Hence, asthma and related pathologies are characterized by a narrowing of airways, varying over short periods of time either spontaneously or as a result of treatment, due in varying degrees to contraction (spasm) of smooth muscle, edema of the mucosa, and mucus in the lumen of the bronchi and bronchioles. Generally, these changes (and thus asthma symptoms) are triggered by the local release of spasmogens and vasoactive substances (e.g., histamine or certain leukotrienes or prostaglandins) in the course of an allergic process. Nonlimiting representative examples of "related pathologies" include non-asthmatic conditions characterized by airway hyper responsiveness (e.g., chronic bronchitis, emphysema and cystic fibrosis).

The effector according to this aspect of the invention, may be administered prior to, at the same time, or after the administration of the bronchodilator. One of skill in the art will appreciate that the specific order of administration of the bronchodilator and the effector of the invention will vary depending on the particular bronchodilator and effector selected. In addition, the timing of the administration of the bronchodilator and the effector may vary from mammal to mammal depending on the particular clinical exigencies of each individual mammal. A skilled practitioner may optimize administration by careful monitoring the patient while altering the timing and/or the order of administration of the bronchodilator and the effector of the invention. Clinical changes relevant to assess the therapeutic effect of treatments according to the invention include reduction in the characteristic symptoms and signs of asthma and related pathologies (e.g, dyspnea, wheezing, cough, bronchial hypersensitivity) and improvement of pulmonary function tests. These are based upon patient's symptoms and physician's observations.

In certain preferred embodiments, the bronchodilator and the effector are admixed prior to administration to the mammal. Thus, in a particularly preferred embodiment, the method of the invention include the administration of a formulation including a $\beta_2$-agonist and of a N-sulfated polysaccharide, preferably heparin. In some preferred embodiments, the formulation comprises a mixture of heparin fragments and one or more $\beta_2$-agonists. Another preferred embodiment comprises the administration of a mixture of a particular heparin fraction and one or more $\beta_2$-agonists. In other preferred embodiments, the bronchodilator and the effector are administrated separately.

Dosages will depend on the condition being treated, the particular compound, and other clinical factors such as weight and condition of the mammal and the route of administration.

The terms "therapeutically effective amount" and "therapeutically effective period of time" are used to denote treatments at dosages and for periods of time effective to achieve the therapeutic result sought. Furthermore, one of skill will appreciate that the therapeutically effective amount of either the bronchodilator or the effector may be lowered or increased by fine tuning and altering the amount of the other component. The invention therefore provides a method to tailor the administration/treatment to the particular exigencies specific to a given mammal. As illustrated in the following examples, therapeutically effective ranges may be easily determined for example empirically by starting at relatively low amounts and by step-wise increments with concurrent evaluation of inhibition.

In those embodiments of the invention in which the effector is unfractionated heparin, a therapeutically effective amount of the effector is from about 1 to about 10 mg per kg body weight per administration. In a preferred embodiment of the invention, the therapeutically effective amount of unfractionated heparin is from about 4 to about 8 mg per kg body weight per administration. In a more preferred embodiment, the dosage of unfractionated heparin will range from about 5 to about 7.5 mg per kg body weight per administration.

In those embodiments of the invention in which the effector is LMWH, a therapeutically effective amount of the effector is from about 10 to about 1000 µg per kg body weight per administration. In a preferred embodiment of the invention, the therapeutically effective amount of LMWH is from about 100 to about 750 µg per kg body weight per administration. In a more preferred embodiment, the dosage of LMWH will range from about 200 to about 500 µg per kg body weight per administration.

In those embodiments of the invention in which the effector is ULMWH, a therapeutically effective amount of the effector is from about 1 to about 500 µg per kg body weight per administration. In a preferred embodiment of the invention, the therapeutically effective amount of ULMWH is from about 10 to about 250 µg per kg body weight per administration. In a more preferred embodiment, the dosage of ULMWH will range from about 20 to about 100 µg per kg body weight per administration.

It will be appreciated by those of skill in the art that the number of administrations of bronchodilators and/or of effectors according to the invention will vary from patient to patient based on the particular medical status of that patient at any given time. Without wishing to limit the invention to a particular number of administrations per day, generally two to four administrations per day are envisioned.

Total dosage of bronchodilators according to the invention are as described in the scientific and medical literature (see for example, Goodman and Gilman's supra at pages 664–665).

In those embodiments in which the effector is heparin, a preferred dosage for standard therapy is in a range of approximately of about 200 units per kg body weight per day to about 5,000 units per kg body weight per day. In another embodiment, the preferred dosage is from about 500 units per kg body weight per day to about 2000 units per kg body weight per day. In a most preferred embodiment, the dosage of about 1,000 units per kg body weight per day (80,000 units). One of skill in the art will appreciate that higher or more frequent doses may be given depending on the clinical condition as well as the response of the particular mammal being treated.

The effectors of the present invention, of which a most preferred embodiment is N-sulfated heparin, can be provided as pharmaceutically acceptable formulations using formulation methods known to those of ordinary skill in the art. These formulations can be administered by standard routes, though preferably administration is by inhalation routes. The formulations include those suitable for oral, inhalation, rectal, ophthalmic, (including intravitreal or intracameral) nasal, topical (including buccal and sublingual), vaginal or parenteral (including subcutaneous, intramuscular, intravenous, intradermal and intratracheal). In addition, the combinations may be formulated with polymers allowing for sustained release of the compound.

For inhalation formulations, the compounds of the present invention may be delivered via any inhalation methods known to those skilled in the art. Such inhalation methods and devices include, but are not limited to, metered dose inhalers with propellants such as CFC or HFA or propellants that are physiologically and environmentally acceptable. Other included devices are breath operated inhalers, multi-dose dry powder inhalers and aerosol nebulizers.

In a preferred embodiment of the invention, administration is effected by means of a pump or squeeze-actuated nebulizer. In more preferred embodiments of the invention, administration is effected by means of a metered dose inhaler or an aerosol dispenser.

Formulations of the present invention suitable for oral administration may be presented as discrete units such as capsules, caplets, gelcaps, cachets, pills, or tablets each containing a predetermined amount of the active ingredient as a powder or granules; as a solution or a suspension in an aqueous liquid or a non-aqueous liquid; or as an oil-in-water liquid emulsion or a water-in-oil emulsion and as a bolus, etc. In a more preferred embodiment, administration is effected by liquid solutions, suspensions or elixirs, powders, lozenges, micronized particles and osmotic delivery systems.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

The formulations of the compositions may conveniently be presented in unit dosage form and may be prepared by conventional pharmaceutical techniques as discussed above. Such techniques include the step of bringing into association the active ingredient, preferably the effector and/or the bronchodilator, and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for administration by inhalation includes formulations of the active ingredient, the bronchodilator and/or the effector, in a form that can be dispensed by such inhalation devices known to those in the art. Such formulations may include carriers such as powders and aerosols. The inhalant compositions used in the present invention may comprise liquid or powdered compositions containing the active ingredient that are suitable for nebulization and intrabronchial use, or aerosol compositions administered via an aerosol unit dispensing metered doses.

Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs.

Suitable powder compositions include, by way of illustration, powdered preparations of the active ingredient thoroughly intermixed with lactose or other inert powders acceptable for intrabronchial administration. The powder compositions can be administered via a dispenser, including, but not limited to an aerosol dispenser or encased in a breakable capsule which may be inserted by the patient into a device that punctures the capsule and blows the powder out in a steady stream suitable for inhalation.

Aerosol formulations for use in the subject method would typically include propellants, surfactants and co-solvents and may be filled into conventional aerosol containers that are closed by a suitable metering valve.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels, lotions and pastes comprising the ingredient to be administered in a pharmaceutical acceptable carrier. A preferred topical delivery system is a transdermal patch containing the ingredient to be administered.

Formulations for rectal administration may be prepared as a suppository with a suitable base comprising, such as, for example, cocoa butter.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, for example via a nasal spray, aerosol, or as nasal drops, include aqueous or oily solutions of the active ingredient.

Formulations suitable for vaginal administration may be presented as pessaries, suppositories, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain antioxidants, stabilizers, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

The first aspect of the present invention also provides methods and compositions that may enhance the effectiveness of bronchodilators administered for the treatment of asthma and related pathologies. The methods according to this aspect of the invention thus provide preferred combinations of effective synergisitic amounts of bronchodilators and effectors of the invention. The term "effective synergistic amount" is used to denote known concentrations of the bronchodilator and of the effector. The effective synergistic amount of bronchodilators and/or the effective synergisitc amount of effector is/are less than the minimum amount(s) found empirically necessary when either the bronchodilator or the effector of the invention are not used in combination, either at the same time, or sequentially.

In a second aspect the invention provides analytical tools for the elucidation of the activation and inhibition of the β-adrenergic receptor activity. The invention provides novel tools to assess the role played by polyanions and their interaction with bronchodilators in the modulation of βARK activity. More specifically, the invention sets forth compositions and methods useful to evaluate the ability of mucopolysaccharides, such as heparin, to inhibit the phosphorylation of the β-adrenergic receptor by βARK. Such tools can be used as "probes" of the physiological function of βARK and of the interplay with agonist-specific desensitization of the receptor-coupled adenyl cyclase system.

In a third aspect the invention provides novel compositions useful for preventing tolerance to medications, such as to bronchodilators, used in the treatment of asthma and related pathologies. This aspect of the invention also provides novel compositions useful for treating asthma and related pathologies in a mammal, including the administration of effectors in conjunction with bronchodilators as described infra. The bronchodilators and the effectors as well as any pharmaceutically acceptable carriers or diluents according to this third aspect of the invention are as described for the first aspect.

Preferred unit dosage formulations are those containing a daily dose or unit, daily sub-dose, as herein above recited, or an appropriate fraction thereof. It should be understood that in addition to the ingredients, particularly mentioned above, the formulations of the present invention may include other agents conventional in the art having regard to the type of formulation in question.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Treatment of Asthmatic Patients

To illustrate the ability of the compositions and methods of the invention to prevent tolerance, asthmatic patients with a history of stable asthma were enrolled in the following experiment(s). All subjects were non-smokers and had no recent history of upper respiratory infection. None of the subjects were taking regular asthma medications (corticosteroids, cromolyn) except a short acting $\beta_2$-agonist as needed. Subjects taking salmeterol (e.g., the formulation sold under the mark Serevent® by Glaxo Wellcome Inc.) at least two weeks prior to enrollment in the study were asked to discontinue the use of salmeterol and change to albuterol (e.g., formulations sold under the mark Proventil® by Schering Corporation, or under the mark Ventolin® by Glaxo Wellcome Inc.) To obtain a dose-response curve for methacholine, measurements of forced expiratory volume in one second ($FEV_1$) were performed before and following methacholine administration. For this purpose, solutions of methacholine were prepared daily by dissolving methacholine in phosphate-buffered isotonic saline solution and delivered by nebulizer (De Vilbiss No. 644, Somerset, Pa.); the mass median aerodynamic diameter of the droplets was 3.9 $\mu$m (geometric SD, 2.4). For bronchial provocation, the nebulizer was attached to a dosimeter, which consists of a breath-activated solenoid valve and a source of compressed air (20 psi). When triggered by the subject's inspiratory effort, the solenoid valve was set to remain open for 0.6 second during inhalation to allow the compressed air to flow through the nebulizer, dispersing an average of 0.023 ml of the solution with each breath. The aerosolized material was delivered from the end expiratory position through the course of a submaximal inspiratory effort. After the baseline measurement of $FEV_1$ the subjects inhaled five breaths of the saline diluent, and the measurements were repeated after a two-minute interval. A dose-response curve for methacholine was then established: subjects took five inhalations from each of the dilutions of methacholine solution at intervals of five minutes; the concentration of the first dilution was 0.075 mg per milliliter, and the concentration of the subsequent dilutions was increased in a doubling manner. Bronchial provocation was stopped when a 20% fall in $FEV_1$ was achieved. The $FEV_1$ was then plotted against the cumulative dose of methacholine expressed in breath units; one breath unit ("BU") is defined as one inhalation of a preparation containing 1 mg of methacholine per milliliter. The results are expressed as the cumulative provocation dose of the methacholine that decreases the $FEV_1$ by 20% ($PD_{20}$).

The study was conducted in a placebo controlled, double blind, randomized crossover design. The study consisted of two 5 day treatment periods; each treatment period was separated by two weeks washout. On day 1, after baseline pulmonary function tests methacholine challenge test was performed to determine the baseline $PD_{20}$. On experiment days 2–5, starting at 08:00, baseline measurements of $FEV_1$ were obtained. Following this, subjects inhaled 4 ml of either a placebo (bacteriostatic injection water) or heparin solution (80,000 units). $FEV_1$ was obtained 45 minutes after the inhalation of the blinded medication (heparin or placebo), and then 2 puffs of salmeterol(50 $\mu$g) were given. Forty-five minutes after dosing with salmeterol, measurements of $FEV_1$ were repeated after methacholine to determine the post-salmeterol $PD_{20}$. On experiment days 2–4, all subjects returned to the laboratory at night (20:00 hour) to receive the blinded medication (placebo or heparin), and forty-five minutes to one hour later, 2 puffs of salmeterol were administered. Baseline $PD_{20}$ was compared to post-salmeterol $PD_{20}$ for demonstration of bronchoprotection. Post-salmeterol $PD_{20}$ on days 2–5 was used to demonstrate tolerance to its bronchoprotective action and its prevention by inhaled heparin.

As shown in FIG. 1 the baseline values of $PD_{20}$-methacholine were comparable on two treatment periods (5.8±1.7 BU vs. 4.0±1.4 BU). During treatment with placebo the first dose of salmeterol caused a marked increase in $PD_{20}$-meth to 60±18 BU (P<0.05), which decreased by 53% to 29±10 BU after the seventh dose (P<0.05) indicating loss of bronchoprotection. In the inhaled heparin phase, $PD_{20}$-meth increased to 78±22 BU after the first dose of salmeterol (P<0.05), but decreased by only 36% to 49±14 BU after the seventh dose (P=NS). The $PD_{20}$-meth values post-salmeterol were greater on heparin vs placebo days (P<0.05). This data indicates that the administration of a representative effector of the invention (e.g., heparin) prevents the development of tolerance to the bronchoprotective effects of a representative bronchodilator of the invention (eg. salmeterol).

Figure 2:
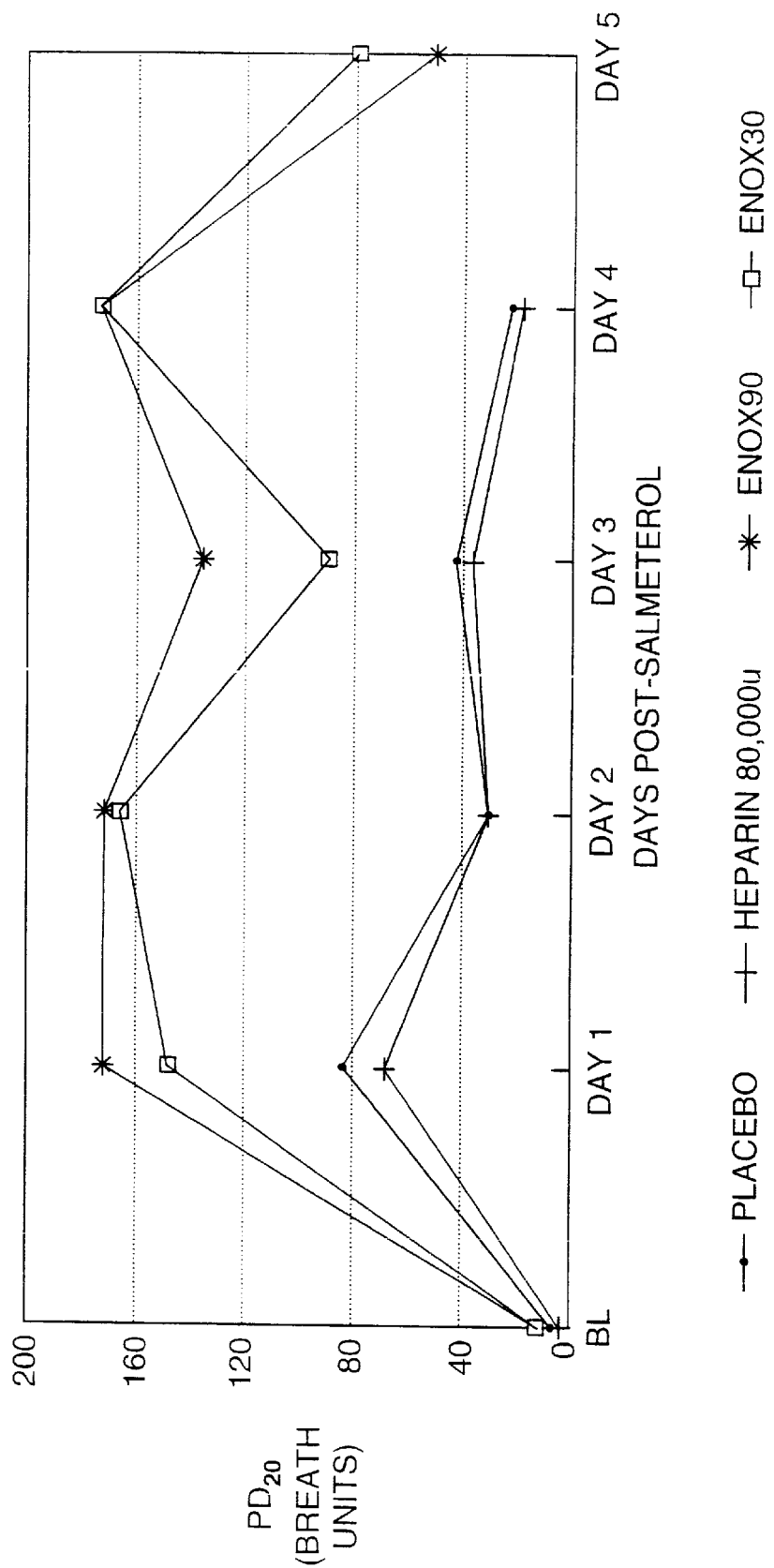
FIG. 2 is a graphic representation showing the ability of a representative, nonlimiting, bronchodilator (salmeterol) used in conjunction with representative, nonlimiting, effectors (low molecular weight heparin preparations) according to the invention to prevent tolerance to bronchodilators in a heparin-nonresponsive patient. Data are shown as the cumulative provocating dose of methacholine in breath units, which caused a 20% decrease in $FEV_1$ ($PD_{20}$). $PD_{20}$ was determined for the baseline day (BSL) and after the $1^{st}$, $3^{rd}$, $5^{th}$, and $7^{th}$ dose of salmeterol (42 μg BID), following pretreatment with inhaled heparin (80,000 units BID), low molecular weight heparin enoxaprin 30 mg or 90 mg or placebo. The first dose of salineterol caused a marked increase in $PD_{20}$-methacholine on day 1, showing bronchoprotection. Lesser bronchoprotection was observed after the $3^{rd}$-$7^{th}$ doses of salemeterol (days 2-4), indicating development of tolerance. As shown tolerance was prevented by inhaled low molecular weight heparin.

In addition, we identified a patient unresponsive to heparin treatment according to the invention (see FIG. 2, showing development of tolerance to the bronchoprotective effects of a representative bronchodilator of the invention (e.g., salmeterol) in conjunction with heparin (identified as ∆—∆) as well as placebo (identified as •—•) treatments). As shown in FIG. 2, treatment of this patient with low molecular weight heparin preparations (30 mg enoxaparin, identified as ■—■) and (90 mg enoxaparin, identified as ◊—◊) resulted in the prevention of tolerance and marked augmentation of the bronchoprotective effects of a representative bronchodilator of the invention (e.g., salmeterol).

It should be understood, of course, that the foregoing relates only to preferred embodiments of the present invention and that numerous modifications or alterations may be made therein without departing from the spirit and the scope of the invention as set forth in the appended claims.

What is claimed is:

1. A method of preventing tolerance to a bronchodilator in a mammal, comprising the administration to said mammal in need of such prevention of therapeutically effective amounts of the bronchodilator and of a sulfated polysaccharide, said sulfated polysaccharide comprising from 1 to about 10 sugar residues.

2. The method of claim 1, wherein the bronchodilator and the sulfated polysaccharide are admixed prior to administration to the mammal.

3. The method of claim 2, wherein the bronchodilator and/or the sulfated polysaccharide are admixed with a pharmaceutically acceptable carrier medium prior to administration.

4. The method of claim 1 wherein the bronchodilator is a $\beta_2$-adrenergic agonist.

5. The method of claim 4, wherein the $\beta_2$-adrenergic agonist is selected from the group consisting of salmeterol, formoterol, bambuterol, albuterol, terbutaline, pirbuterol, bitolterol, metaproterenol, isoetharine, and isoproterenol.

6. The method of claim 4, wherein the $\beta_2$-adrenergic agonist is salmeterol.

7. The method of claim 1, wherein more than one bronchodilator is administered.

8. The method of claim 1, wherein the sulfated polysaccharide is selected from the group consisting of tetrasaccharides, pentasaccharides, hexasaccharides, septasaccharides, octasaccharides, nonasaccharides, and decasaccharides.

9. The method of claim 8, wherein the sulfated polysaccharide is an N-sulfated tetrasaccharide.

10. The method of claim 1, wherein the sulfated polysaccharide is a low-molecular weight heparin (LMWH).

11. The method of claim 1, wherein the sulfated polysaccharide is an ultra-low molecular weight heparin (ULMWH).

12. The method of claim 11, wherein the ULMWH comprises at least one heparin fraction selected from the group consisting of tetrasaccharides, pentasaccharides, hexasaccharides, septasaccharides, octasaccharides, nonasaccharides and decasaccharides.

13. The method of claim 11, wherein the ULMWH comprises a tetrasaccharide.

14. The method of claim 1, wherein more than one sulfated polysaccharide is administered.

15. The method of claim 11, wherein the ULMWH has substantially no anticoagulant activity.

16. The method of claim 10, wherein the LMWH has substantially no anticoagulant activity.

17. The method of claim 1, wherein the administration is by inhalation, oral, sublingual, transdermal, parenteral, topical, intrarectal, intrabronchial, intranasal, or is intraocular.

18. The method of claim 17, wherein administration by inhalation is accomplished using a metered dose inhaler.

19. The method of claim 17, wherein administration by inhalation is accomplished using a breath operated inhaler.

20. The method of claim 17, wherein administration by inhalation is accomplished using a multidose dry powder inhaler.

21. The method of claim 17, wherein administration by inhalation is accomplished using an aerosol nebulizer.

22. The method of claim 17, wherein parenteral administration is intravenous or intramuscular.

23. The method of claim 1, wherein the bronchodilator and the sulfated polysaccharide are in powder form.

24. A method of treating asthma and related pathologies in a mammal, comprising the administration to said mammal in need of such treatment of therapeutically effective amounts of a bronchodilator and of an a sulfated polysaccharide, said sulfated polysaccharide comprising from 1 to about 10 sugar residues.

25. The method of claim 24, wherein the bronchodilator and the sulfated polysacharide are admixed prior to administration to the mammal.

26. The method of claim 25, wherein the bronchodilator and/or the sulfate polysaccharide are admixed with a pharmaceutically acceptable carrier medium prior to administration.

27. A composition for the treatment of asthma and related pathologies in a mammal, comprising therapeutically effective amounts of a bronchodilator and of a sulfated polysaccharide, said sulfated polysaccharide comprising from 1 to about 10 sugar residues.

28. The composition of claim 27, further comprising a pharmaceutically acceptable carrier.

29. The composition of claim 27, wherein the bronchodilator is a $\beta_2$-adrenergic agonist.

30. The composition of claim 27, wherein the $\beta_2$-adrenergic agonist is selected from the group consisting of salmeterol, formoterol, bambuterol, albuterol, terbutaline, pirbuterol, bitolterol, metaproterenol, isoetharine, and isoproterenol.

31. The composition of claim 30, wherein the $\beta_2$-adrenergic agonist is salmeterol.

32. The composition of claim 27, wherein the sulfated polysaccharide is an N-sulfated polysaccharide.

33. The composition of claim 32, wherein the N-sulfated polysaccharide is heparin.

34. The composition of claim 33, wherein the N-sulfated polysaccharide is an ultra-low molecular weight heparin (ULMWH).

35. The composition of claim 32, wherein the N-sulfated polysaccharide is a low molecular weight heparin (LMWH).

* * * * *